United States Patent [19]
Schopper et al.

[11] Patent Number: 5,452,076
[45] Date of Patent: Sep. 19, 1995

[54] FLUID DETECTION SYSTEM

[75] Inventors: Milton D. Schopper, Houston; James L. Taylor, III, Katy; Paul R. Bennett, Jr., Houston, all of Tex.

[73] Assignee: Optiguard, Inc., Spring, Tex.

[21] Appl. No.: 128,601

[22] Filed: Sep. 29, 1993

[51] Int. Cl.6 ............................................. G01N 21/41
[52] U.S. Cl. ..................................... 356/128; 356/133
[58] Field of Search ............... 356/128, 133, 135, 136, 356/137; 250/577, 900, 904, 905, 907

[56] References Cited

U.S. PATENT DOCUMENTS 4,907,878  3/1990  Arditty et al. ...................... 356/133

*Primary Examiner*—F. L. Evans
*Attorney, Agent, or Firm*—Robert L. Graham

[57] ABSTRACT

The present invention relates to a fluid detection system which can be adapted for use in applications including liquid-level detection, pipeflow monitoring, and interstitial leakage in double-walled containers. The system operates on principles of optics and provides the capability of remotely differentiating between fluids having different refractive indices including liquids and vapors. The present detector uses a unique light pulsation technique which increases permissible operating ranges over existing optical detection systems.

15 Claims, 3 Drawing Sheets

FLUID DETECTION SYSTEM

BACKGROUND OF THE INVENTION

This invention relates to a device for detecting the presence of fluids in conduits or containers. In one aspect the invention relates to an optical sensor system which is responsive to the index of refraction of the fluid. In another aspect, the invention relates to an optical sensor system which can distinguish between fluids having different indices of refraction including vapors and liquids.

The ability to remotely monitor fluids is important in many industrial applications. Moreover, there are a number of applications which require the ability to differentiate between fluids. Liquid level detectors, and the like, represent common examples of systems which operate on the principle of differentiating between fluids. In another example, product pipelines are often used to transport different fluids in slugs or batches, and it is important to identify the interface between the batches so that valving can be controlled to minimize cross-contamination of the fluids. Other applications include leak detection in the interstitial space of double-walled containers used to store hydrocarbons or other petrochemicals. In interstitial leak monitoring, water is often intermittently present due to condensation or the invasion of rain and snow, and the ability to distinguish water from a hydrocarbon would eliminate false leakage alarms, and provide an indication of the actual condition of the inner lining of the container.

A number of devices which employ optical-type sensors for the purpose of remotely detecting the presence of fluids in pipelines, tanks, vessels, and the like have been developed. Typically these devices comprise the components of a light source, an optical-type probe placed at the location where the fluid is to be detected, a light detector element, and fiber optics which optically connect the source, the probe, and the detector in series. In normal operation, the source will send light to the probe via the transmission line and the probe will in turn transmit light to the detector at a predetermined intensity level thus indicating normal operation. For detecting the presence of a fluid, the probe will have an optical property which undergoes a change as its environment changes from one fluid to another (e.g. from air to water), so that the light returned from the probe to the detector will be attenuated or otherwise disrupted to indicate the presence of the fluid to be detected.

U.S. Pat. No. 5,187,366 describes an optical sensor which operates on the principles described above and is designed to detect leakage into the interstitial spaces of double-walled containers. The probe comprises a first and second optic fibers aligned in end-to-end relation and separated by a small gap. In normal operation light emitted by the source travels through the first optic fiber, across the gap, and through the second fiber to the detector. The fiber optic ends of the probe are held in alignment using a coating of a material which is soluble in the fluid to be detected. Upon exposure to the fluid the coating dissolves and the ends of the first and second fibers are induced to move out of optical alignment, thereby disrupting the flow of light from the emitter to the detector indicating the presence of the fluid. A mechanical spring is used to bias the probe fiber ends apart to ensure the misalignment of the fibers as the coating dissolves.

U.S. Pat. No. 5,200,615 describes an optical sensor which uses a probe comprising a first and second optic fibers having ends in parallel relation which are embedded within a soluble phosphorescent coating. Light sent to the probe from the source via the first fiber is absorbed by the phosphorous material and re-emitted. The re-emitted light illuminates the end of the second fiber and travels therethrough to the detector to indicate normal operation. Upon exposure to the fluid to be detected the soluble coating dissolves and the phosphorous material is dispersed thereby disrupting the flow of emitted light to the detector.

U.S. Pat. No. 5,200,615 further teaches the use of a probe comprising a single optic fiber having a core and cladding. The probe is formed by stripping a small length of the cladding off to expose the core, and applying a phosphorescent soluble coating around the core. As the coating dissolves and the phosphorous material is disbursed the light intensity at the detector is attenuated thereby indicating the presence of the fluid. A disadvantage of the sensors of U.S. Pat. 5,187,366 and 5,200,615 is that the soluble coating must be replaced after exposure to the fluid to be detected.

An optical device for measuring the level of liquid in a container is described U.S. Pat. No. 4,641,025. The device comprises a light pulse source such as a laser diode, an on/off type optical detector, and a plurality of probes connected between the source and detector by fiber optics. Each probe attenuates the light traveling from the source to the detector by an amount proportional to the index of refraction of the fluid surrounding the probe. A plurality of such probes are positioned along a line which intersects the boundary between the liquid and vapor in the container, so that in operation a number of probes will be positioned in the vapor above the liquid (typically air) and the remaining probes will be immersed in the liquid. The light pulse source is provided with a timing circuit to send light pulses of equal intensity to the probes sequentially, producing an attenuated sequence of pulses transmitted to the detector. Because the vapor has a lower index of refraction than the liquid, the intensity of the light transmitted to the detector via the probes in the vapor is higher than the light transmitted via the probes in the liquid. The detector is provided with a threshold circuit such that the detector produces an outgoing electrical analog pulse corresponding only to an incoming light pulse having an intensity above a predetermined threshold. Light pulses received below the threshold intensity produce no analog pulse. The threshold is set between the intensity of the light pulses transmitted by the probes in the vapor and that transmitted by the probes in the liquid, and thus only probes located in the vapor result in an electrical analog pulse at the detector. The analog pulses can be counted to determine the number of probes in the vapor and thereby determine the location of the liquid level. The device of U.S. Pat. No. 4,641,025 would not appear to be directly applicable to monitoring fluids in a flowing environment such as a pipeline.

SUMMARY OF THE INVENTION

The apparatus and method of the present invention provide a reliable, sensitive, low cost optical fluid sensor for monitoring and differentiating between fluids. It is an object of the invention to provide the capability of remotely differentiating between fluids having different indices of refraction including vapors and liquids, so that the presence of these fluids may be unambiguously ascertained. The invention is applicable to highly transient environments such as fluids flowing through pipelines, as well as liquid level measurement, and preventative applications such as interstitial leakage monitoring. The term fluid hereafter is understood to refer to both gases (vapors) and liquids.

The present invention can, in principle, differentiate between a large number of fluids having different refractive indices. However, in most practical applications it is generally known what fluids will potentially be present and, therefore, the present invention can be tailored or calibrated to target the detection of those particular fluids. For example, it may be desired to monitor a pipeline used in intermittently conducting slugs or batches of various known liquids such as hydrocarbons and/or aqueous liquids. Alternatively, the objective may be the detection and differentiation between air, ground water, or oil in the interstitial space of a double-walled oil storage tank.

The system of the present invention comprises a variable intensity light pulse source such as an LED or laser diode having an intensity proportional to input electrical signal (current or voltage), a photodetector, an optical probe, and fiber optics for connecting the probe in series between the source and the detector. The photodetector may be a photodiode in combination with a threshold or gate-type electrical circuit having an electrical output which may be interpreted analogously as on or off. In a preferred embodiment, the light pulse source is controlled to permit the generation of pulses of known intensity in a predetermined sequence.

In accordance with the present invention, a variable intensity light source produces a series of light pulses which vary in intensity from pulse-to-pulse (as in a mathematical ramp function or other predetermined sequence). A refractometer probe having an optical property responsive to the index of refraction of the ambient fluid is positioned at a point where the fluid is to be detected, or differentiation between two or more fluids is to be ascertained. A photodetector is provided which has a threshold activation level of intensity whereby an incoming light pulse having an intensity above the threshold produces an on indication, and below the threshold an off indication. As described below, the probe in contact with the fluid is of the type which attenuates light passing therethrough in proportion to the index of refraction of the ambient fluid surrounding the probe. The attenuation is associated with the physical principles describing the angle of total reflection at the interface of a transparent solid and a fluid.

Prior to installation, the sensor will be calibrated for each fluid which may be encountered during operation by immersing the probe in the fluids one-by-one and measuring the activation light as a function of light received by the detector from the LED. Because each fluid will have a different index of refraction, there will be a different value of the activation light intensity emitted from the LED, which in one embodiment is a function of current to the LED, termed the "activation current". The probe of the sensor will then be mounted for contacting the fluid to be identified and the activation current corresponding to the fluid will be measured. The measured activation current for the fluid to be identified is then correlated with the calibration activation current data to identify the fluid.

As mentioned previously, the system of the present invention has many applications including liquid level controls, interface controls, fluid detectors in flowing fluids, interstitial fluid detection, etc. It is particularly applicable to hazardous installations (e.g. hydrocarbon tanks), where the use of electrical sensor systems would require explosion proof electrical switches. Because the present refractometer probe and leads connecting the probe to the light source and detector are not electrical, no special explosion prevention means are necessary. Furthermore, the leads may be long permitting the electrical components of the present system to be positioned at safe locations.

All of the applications cited above involve the presence of a particular fluid (A) during normal operation, and due to operational factors there exists the potential for the presence of some other fluid (B) having a different index of refraction than (A). Prior to installation, the probe of the present fluid detection system will be independently calibrated for both fluids so that the activation current for each fluid is known. Accordingly, the minimum and maximum intensity limits of the light pulses from the source are adjusted to encompass both activation levels. In operation, the light source is operated cyclically and the activation current for each cycle monitored. During normal operation the activation current will correspond to that for fluid (A). A change in the activation current from that for fluid (A) to the activation current corresponding to fluid (B) would signal a change in the fluid surrounding the probe from fluid (A) to fluid (B). It would likewise be possible to detect the presence of additional fluids having different refractive indices than either (A) or (B). Of course, the probe would also have to be independently calibrated for each fluid to be detected. A variation of the system involves calibrating for only one fluid (A), and monitoring to detect a change in activation level, indicating a change from fluid (A) to an unknown fluid in contact with the probe.

The fluid sensor system of the present invention can be easily incorporated into electronic controls for fluidic systems and the output of the sensor can serve as a basis for sounding warning devices, or activating valves or pumps, as the case may be.

DESCRIPTION OF THE PREFERRED EMBODIMENTS

The fluid sensor system of the present invention is described in detail below by considering the components of the sensor system, the principles by which the sensor system is calibrated for differentiating between fluids having different refractive indices, and operation of the sensor system.

Fluid Sensor System

Figure 1:
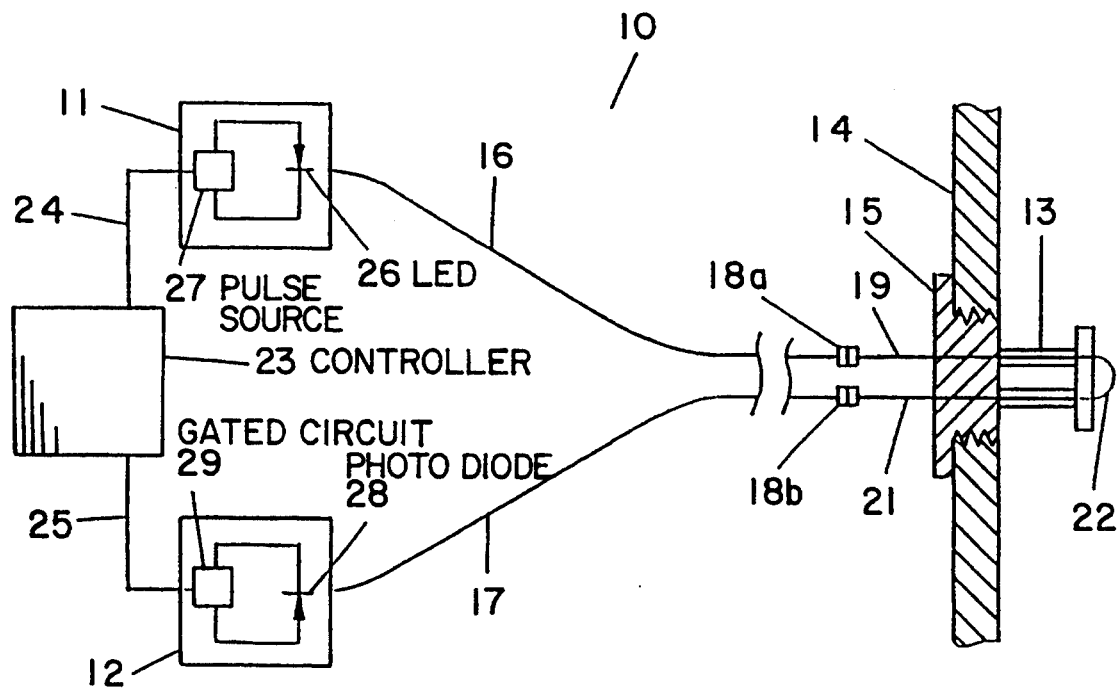
FIG. 1 is a schematic diagram of the present fluid sensor system.

FIG. 1 illustrates the fluid sensor system 10 of the present invention as comprising variable intensity light pulse source 11, light detector 12, probe 13, and light transmission lines 16 and 17. Probe 13 is mounted in a wall of vessel 14 using sealing bushing 15. Probe 13 comprises an integral optic transmission line bent to form inlet line 19, outlet line 21, and U-shaped sensor tip 22 contacting the fluid contained within vessel 14. Light source 11 is connected via line 16 to probe inlet line 19 using connector 18a, and light detector 12 is connected via line 17 to probe outlet line 21 using connector 18b. As can be seen in FIG. 1, light pulses emitted from source 11 travel through line 16, through probe inlet line 19, through probe tip 22, through probe outlet line 21, through line 17, and are received by detector 12. Microprocessor controller 23 is connected to light source 11 and detector 12 by electrical cables 24 and 25, respectively. In practice, light source 11, detector 12, and microprocessor 23 may be mounted in a single housing (not shown) as a unit.

Light pulse source 11 comprises a light emitting diode (LED) 26 and preferably has a light intensity output proportional to input current or voltage. Light emitting diodes such as the High Power AlInGaP Greenish-Yellow (HLMA-CP00) LED marketed by Hewlett Packard may be used. In the preferred embodiment, LED 26 is powered by variable current pulse source 27.

Transmission lines 16 and 17, and probe 13 comprise fiber optics and may be either polymer or glass fibers with the former being preferred. Polymer fibers manufactured by Toray Industries (marketed under the name of Raytela Polymer Optical Fibers) have been shown to be suitable for use in the present invention. These are step index fibers with a diameter on the order of 1.0 mm comprising a polymethacrylate core having an index of refraction of 1.49 and a fluorinated polymer cladding with index of refraction of 1.42.

Detector 12 may be an on/off type photodetector having a predetermined threshold level of intensity such that an incoming light pulse having an intensity below the threshold produces an off indication, and a pulse having an intensity above the threshold produces an on indication. Detector 12 may be a photodiode 28 (such as those manufactured by EG&G Vactec, Model No. VTB8440-B) operating in combination with a threshold or gated electrical circuit 29. Photodiodes of the type cited above produce an electrical current and voltage proportional to the intensity of light incident upon the diode. The associated detector circuitry 29 may comprise a constant voltage source connected to a gated output line such that for a diode output voltage below a predetermined threshold the gate is open (open-circuited) producing an analog off indication, and for a diode output above the threshold the gate is closed thereby short-circuiting the constant voltage source to the detector output line 25 to produce an analog on indication. The on/off indication may be either an electrical analog or digitized signal.

Microprocessor 23 may be used to control the intensity and frequency of pulses of light emitted from LED 26 by controlling via cable 24 the amperage and frequency of electrical current pulses sent to the LED from current supply 27. Thus, at all times during the operation of the sensor the electrical current input to the LED is known. Microprocessor 23 may be programmed for driving light source 11 to produce a series of light pulses having a prescribed frequency and intensity variation. The duration of each light pulse may range between 50 to 500 microseconds, preferably 50 to 200 microseconds, and the cyclic frequency may range between 0.05 to 1.0 cycle per second (one complete cycle of a predetermined sequence). Microprocessor 23 also serves to monitor the on/off status of detector 12 by monitoring the output of circuit 29 via cable 25. Microprocessor technology required to control light source 11 and to monitor the output of detector 12 is within the ordinary skill of those in the pertinent art. Also with the ordinary skill is the ability to apply a single microprocessor to operate multiple sensors of the present type in parallel.

An important aspect of the present invention is the pulsed operation of LED 26, as opposed to a continuous illumination. The pulsed operation allows the LED to be operated at higher output intensities than is possible with continuous illumination without exceeding the recommended current duty cycle of the LED. Due to attenuation inherent in all fiber optics, higher light source intensities permit operation over longer lengths of transmission lines 16 and 17, and also permit the use of refractive index sensors possessing wider dynamic ranges.

Also of importance for increasing acceptable fiber optic lengths is the spectral matching of the wavelength for maximum intensity output of LED 26 to the wavelength of minimum attenuation of fiber optics 16 and 17 and probe 13. The particular LED and polymer fiber optics cited above exhibit good spectral matching characteristics. For example, the Greenish-Yellow LED has its peak emission at a wavelength of 573 nm (nanometer), while the Raytela step index fiber exhibits its minimum attenuation of 0.07 dB/m at very nearly this same wavelength. For this configuration, the permissible combined lengths of lines 16 and 17 may be between 200 to 400 meters. It should be noted that most optical-type fluid sensors in use presently are limited to ranges below about 25 meters. The cited Hewlett Packard LED, the Raytela fiber, and EG&G Vactec photodiodes are intended to be representative only of the numerous possible light source and optical fibers, and detectors which can be combined for use in the present fluid sensor.

Figure 2:
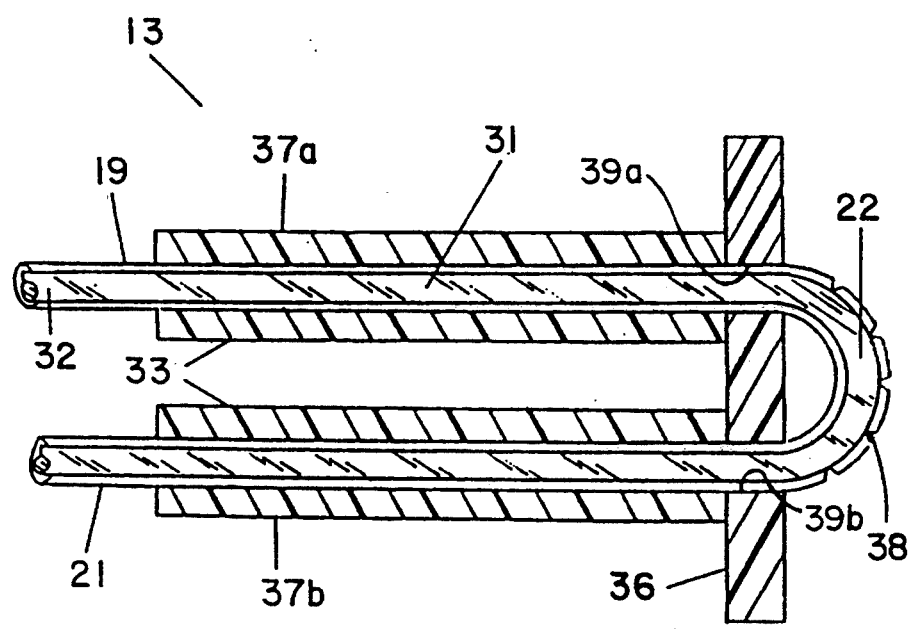
FIG. 2 is a longitudinal sectional view of the probe of the present sensor system.

As best seen in FIG. 2, probe 13 comprises an integral light transmitting fiber 31 having inlet line 19, outlet line 21, and U-shaped tip 22. Fiber 31 may be a glass fiber optic or a polymer fiber optic of the type described above, and has core 32 surrounded by a cladding 33. The end of line 19 is held juxtapose to the proximate end of fiber optic 16 by connector 18a (see FIG. 1), and the end of line 21 is juxtaposed to the proximate end of fiber optic 17 by connector 18b. Connectors 18a and 18b may be any type connectors which optically align the aforementioned transmission lines.

Probe lines 19 and 21 are inserted through plastic disk 36 which maintains the shape of tip 22. Lines 19 and 21 are provided with jackets 37a and 37b which protect the lines during installation and operation. Probe 13 is mounted in a wall of vessel 14 using bushing 15 threaded sealingly into the vessel wall. Lines 19 and 21 pass sealingly through bushing 15 and may be sealed and fixed to the bushing using adhesives (not shown). The cladding may consist of Teflon (tetrafluoroethylene) and the jackets of HDPE.

Probe tip 22 has a plurality of regions 38 wherein cladding 33 is disrupted thus exposing the core 32 to the ambient fluid. A light pulse generated at source 11 is transmitted through line 16, enters the probe through line 19, and is transmitted to tip 22 where a fraction of the light is lost through the exposed regions of the core into the surrounding fluid. The remaining light is transmitted from the tip, through line 21, through line 17, and to detector 12.

The degree of light attenuation in tip 22 is a function of several geometric factors including the bend radius of the tip and the surface area of the exposed core regions 38. However, for a probe of given geometry and core exposure the degree of attenuation depends predominantly on the index of refraction (n) of the fluid surrounding the tip 22 and contacting exposed regions 38. This dependence is described by the physical principle of the angle of total internal reflection at the interface of a transparent solid and fluid which states that the attenuation will increase with the index of refraction of the fluid. Thus for a particular intensity. light input to the probe, the attenuation from tip 22 in air (n=1.00) will be less than for water (n=1.33), which in turn will be less than that for the tip immersed in a hydrocarbon (n=1.45, typical). The present novel fluid sensor provides a calibrated device for measuring the attenuation level and thereby identify the particular fluid present at the probe tip. In this aspect, the probe Operates as a refractometer probe.

In assembling the refractometer probe 13, the exposed core regions 38 can be formed by cracking cladding 33 as lines 19 and 21 are drawn through holes 39a and 39b in disk 36. As the lines are completely drawn into the disk, the severity of the bending in tip 22 is sufficient to induce tensile stresses along the outer part of the tip which crack cladding 33 to expose core 32 and form exposed regions 38. It has been found by this method that depending upon the fiber-to-tip bending radius, approximately 10 to 40% of the outer surface of the core is exposed. Tests have shown that these core exposure levels are sufficient to operate the present fluid sensor. Importantly, precise control over the core exposure is not necessary since the probe is calibrated, as will be described, after the cracks have been formed. It should be noted that the core 32 itself does not crack since the core is an integral fiber with a diameter on the order of 0.98 mm, while the cladding 33 is a thin coating with a thickness on the order of 0.01 mm.

As has been stated, the light attenuation is dependent on the bend radius of tip 22. In general, smaller bend radii will induce more light attenuation thereby giving a wider dynamic range for identifying fluids having numerically similar indices of refraction, such as two liquids. Larger bend radii are suitable for resolving refractively dissimilar fluids such as a vapor and a liquid. Thus, the exact probe geometry will vary from application to application. The following table gives preferred ranges of sensor characteristics for applications requiring the resolution and identification of three fluids consisting of air, water, and a hydrocarbon. These ranges are for operation with the Hewlett Packard LED, the Raytela polymer optical fiber, and EG&G Vactec photodiode cited above.

| Range | Broad Range | Preferred Range | Most Preferred |
|---|---|---|---|
| Probe Tip Bend Radius (mm) | 2 to 8 | 2 to 6 | 2 to 4 |
| Percent of Core Exposed in | 5 to 50 | 10 to 40 | 15 to 35 |

-continued

| Range | Broad Range | Preferred Range | Most Preferred |
|---|---|---|---|
| Probe Tip (%) | | | |

As mentioned previously, the length of the leads 16 and 17 may vary within wide limits, ranging from a few centimeters to several hundred meters. For hazardous environments, the leads will generally be from 15 to 100 meters.

For the preferred ranges given above, the following table gives experimental data showing the resolution of the sensor with the probe tip contacting various fluids. These data indicate the intensity or power of light transmitted from the probe 13 to the detector 12 for a light source 11 having an emission power of 100,000 nano-Watts (nW). These data show the effect of fluid index of refraction on the light attenuated at the probe tip 22. It is important to note excellent resolution of the sensor from fluid-to-fluid.

| Fluid Type | Power of Attenuated Light (nW) at the Detector for a Light Source Emission Power of 100,000 nW |
|---|---|
| Air (n = 1.0) | 13,497 |
| Water (n = 1.33) | 8,745 |
| Alcohol (n = 1.36) | 5,707 |
| Gasoline (n = 1.42) | 1,698 |
| Diesel Fuel (n = 1.46) | 237 |
| Furnace Oil (n = 1.49) | 6 |

While the present invention has been described in terms of a U-shaped probe tip, other tip geometrics, such as a spiral shape having multiple turns are possible without departing from the present inventive concept.

Calibration and Fluid identification

The calibration of the fluid detection system of the present invention will be described with reference to an electrically (current) operated LED. It is to be understood, however, that any light pulse source having an output proportional to a measurable input signal may be used.

As has been described, microprocessor 23 controls the amperage of electrical current pulses sent from current source 27 to LED 26 and thereby controls the intensity of light pulses sent to probe 13. The light pulses are attenuated at probe tip 22 in proportion to the refractive index of fluid contacting the probe tip. Thus, light pulses of diminished intensity are received at detector 12.

Detector 12 is designed to have an on/off status such that an incoming light pulse having an intensity below a predetermined threshold produces an off indication, whereas a pulse having an intensity above the threshold produces an on indication. It can be appreciated, therefore, that the current input to the LED required to activate the detector will increase as the index of refraction of the fluid contacting the probe increases. This current is herein referred to as the activation current.

For calibrating the present sensor, the probe may be immersed in a particular fluid, and the current to the LED increased incrementally from zero until the activation current is achieved. For any particular application, the calibration process will be repeated for each potentially present fluid and the activation current for each fluid recorded as calibration data. The calibration process can be carried out with the configuration of FIG. 1 since at any instant, the microprocessor monitors both the current into the LED as well as the on/off status of the detector.

For the preferred sensor specifications tabulated above, the following table gives representative activation currents for air, water, and a typical hydrocarbon:

| Fluid Type | Activation Current (mA) |
|---|---|
| Air | 60 |
| Water | 210 |
| Hydrocarbon Liquid | 460 |

Notice above the excellent resolution of activation current with fluid type. The sensor can likewise be easily calibrated for other fluids not listed above.

Since the light output of most light sources (including all LED's) varies with temperature, some means of compensating for temperature effects must be employed. In the context of the present invention, this means that if the LED temperature during operation differs from the LED temperature at which the sensor was calibrated, there will be a corresponding shift in activation current for each fluid to be monitored. Because the LED light output is inversely proportional to temperature, the required activation current will increase for LED operating temperatures above the calibration temperature. Two methods for temperature compensation have been developed and are described below.

In the first temperature compensation method, the temperature at LED 26 is directly measured using an electronic temperature sensor (not shown) which is interfaced with microprocessor 23. The calibration activation current data are mathematically compensated for temperature effects using a computer algorithm based on results of experimental tests which have measured LED output as a function of temperature. For example, suppose that the LED 26 operating temperature is above the calibration temperature and experiments have shown that at the operating temperature an additional 5 mA must be supplied to the LED to achieve the same output as at the calibration temperature. Accordingly, the calibration activation current data stored in the microprocessor memory would be shifted up by 5 mA. Variations of this approach are possible without departing significantly from the central concept.

In a second temperature compensation method, a "reference" LED (not shown) is provided which is placed in close proximity to an active LED 26 to be compensated so that both are at the same temperature. The reference LED is connected via an internal optical path to a detector. The internal path provides a fixed level of attenuation and a corresponding fixed value of reference activation current. The activation current for the active LED 26 can be normalized to the reference activation current to compensate for temperature effects. In other words, if the reference activation current increases by 5 mA due to a temperature increase, the active sensor output is adjusted by the same amount.

Similar methods as those outlined above are also employed for compensating the photodiode 28 output for temperature effects. In fact, because the LED 26 and photodiode 28 are typically mounted in close proximity, they will generally operate at the same temperature so that the LED/photodiode pair may be compensated simultaneously.

The operation of the present sensor includes a very simple method for monitoring the system integrity. Because the upper operating limit of the light source is set above the activation levels of all potentially present fluids, it is assured that one of the fluids will be detected when varying the source output from zero to the upper limit. If a fluid is not detected (i.e. the detector is never activated), this provides an indication of a system failure which may include a faulty light source or detector, or a break in the optic fibers.

For automating the operation of the present sensor, the calibrated activation current data can be stored in the memory of microprocessor 23 and during operation can be compared with instantaneously measured activation current levels to identify the fluid present at the probe. Embodied below are three modes of fluid identification which differ by way of the series of current pulses sent to LED 26 for determining the activation current.

Sequencing of the Light Source

The probe of the monitoring system is mounted in a vessel wherein the fluid contacting the probe is unknown, but will be either a gas, water, or a hydrocarbon. The calibrated sensor system will function to identify which of the fluids is present.

Microprocessor 23 may be programmed to send a predetermined series or sequence of current pulses to LED 26 resulting in a corresponding series of light pulses transmitted to probe 22 where each pulse is attenuated as has been described. Each attenuated pulse arriving at detector 12 will produce either an off or on indication which is monitored by microprocessor 23.

The sequencing excitation of the light source may be according to a variety of modes designed to locate with the necessary precision the intensity or the source required to activate the light detector. These modes will be described and referred to as: Ramp Pulse Mode, Reverse Ramp Pulse Mode, and Interpolation Pulse Mode. All of these modes operate to accurately determine the activation signal. The required sensitivity (e.g. the change in current from pulse-to-pulse) will depend on the relative magnitudes of the activation currents for each fluid under investigation. With reference to the Ramp Pulse Mode (FIG. 3), for fluids having activation currents of 60 mA (air), 210 mA (water), and 460 mA (hydrocarbon liquid), the difference between each pulse ($\Delta$) should be small enough so that the activation current of the light detector is unambiguous. Likewise, the Interpolation Pulse Mode (described below) will unambiguously locate the activation level of the light detector for the fluid in contact with the probe. The detection of fluids having a large difference in their refractive indices permits the use of less sensitive (larger changes in current from pulse-to-pulse pulsing than fluids having close refractive indices.

As a general rule, the difference in pulses in the activation region should be $\frac{1}{3}$, preferably 1/5, and most preferably 1/10 the difference between the calibrated activation levels of the first fluid and secondary fluids. For example, the current pulses (proportional light intensity pulses) for differentiating between water (activation at 210 mA) and oil (activation at 460 mA) should preferably differ by less than 25 mA. Pulse differences of 5 mA should be satisfactory for most applications. Activation of the light detector within the activation region constitutes the "threshold intensity" of light or the analog signal of the light intensity (e.g. current or voltage, referred to as "threshold current"or "threshold signal").

Figure 3:
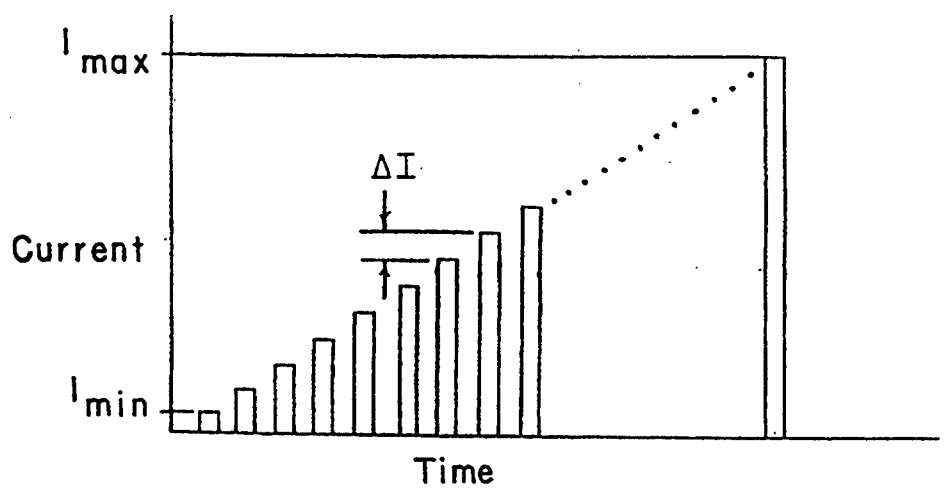
FIG. 3 is a diagram illustrating the ramp pulse mode of operating the present sensor system.

In the Ramp Pulse Mode of operation, the series of current pulses is illustrated graphically in FIG. 3 as comprising pulses ramping between prescribed limits of $I_{min}$(5 mA, typical) and $I_{max}$(600 mA, typical), increasing incrementally by $\Delta I$ (5 mA, typical) from pulse-to-pulse. After each current pulse is sent and the corresponding light pulse is received by detector 12, the on/off status of the detector is polled by the microprocessor. Because the lower current limit of the ramp ($I_{min}$) is set to lie below all possible activation currents, the detector will always register off at the beginning of the ramp. The upper limit of the current ramp ($I_{max}$) is set to lie above all possible activation currents and thus the detector will switch from on to off at some intermediate point in the ramp. At the instant the detector is activated, the current level (activation current) is measured by microprocessor 23 and compared with calibration data stored in the memory of the microprocessor for fluid identification. Referring to the particular calibration activation current data above, for example, it can be seen that if during the ramp the detector switches from off to on at a current level of 210 mA, it can be concluded that water is present at the probe. On the other hand, if the detector remains off until the current level reaches 460 mA, the hydrocarbon is known to be present.

During operation, the microprocessor can be programmed to repeat the ramp sequence cyclically to provide continuous fluid identification. Requisite microprocessor logic steps and peripheral electronic hardware (valve actuators, pumps, etc.) can be provided to invoke responsive measures upon identification of a particular fluid as the case may be. It should be noted that modern microprocessor technology allows the ramp sequences and detector polling to be repeated at very high speeds thereby providing rapid fluid identification. It is also within the ordinary skill to apply a single microprocessor processor to simultaneously operate in parallel multiple sensors of the type described herein.

A variation of the Ramp Pulse Mode is the Reverse Ramp Mode which sequences the pulses from maximum to minimum. The activation of the photodetector occurs at the activation of the switch from on to off.

The Interpolation Pulse Mode is designed to provide a very rapid determination of activation current and fluid identification. Whereas in the ramp mode the current pulses are sent to the LED without regard to the detector status, the interpolation mode invokes a logic step programmed into microprocessor 23 which adjusts the current sent to the LED in response to the instantaneous off or on detector status. An off status results in an increase in LED current, whereas an on status results in a decrease in current. The logic pattern is designed so that the adjusted current will rapidly converge onto the actual activation current corresponding to the fluid at the probe. The software for implementing the Interpolation Mode is well within the ordinary skill in the art.

For illustration purposes, consider that the probe operates in an environment with the potential occurrence of either air (activation current=60 mA), water (210 mA), or a hydrocarbon (460 mA), and that the range of current pulses sent to the LED will lie between 0 and 600 mA. The following series of pulses illustrate two cycles of pulses in the Interpolation Mode. Between the first and second cycles, however, the fluid at the probe has changed from air to the hydrocarbon and the sensor responds to provide this indication. Note that each cycle begins with a current to the LED of 300 mA and is then adjusted up or down depending on the instantaneous detector status, so that if the detector is off the current is increased and if the detector is on the current is decreased. The current is adjusted by progressively smaller amounts in such a way as to cause the current sent to the LED to converge rapidly onto the activation current of the fluid at the probe.

| Cycle 1: Probe Immersed in Air (A.C. = 60 mA) | | |
|---|---|---|
| Calculation of Current | Current to LED | Detector Status |
| Pulse 1 = 0 + (600/2) = | 300 mA > A.C. | ON |
| Pulse 2 = 300 − (600/4) = | 150 mA > A.C. | ON |
| Pulse 3 = 150 − (600/8) = | 75 mA > A.C. | ON |
| Pulse 4 = 75 − (600/16) = | 37 mA < A.C. | OFF |
| Pulse 5 = 37 + (600/32) = | 55 mA < A.C. | OFF |
| Pulse 6 = 55 + (600/64) = | 64 mA > A.C. | ON |
| Pulse 7 = 64 − (600/128) = | 59 mA < A.C. | OFF |
| Pulse 8 = 59 + (600/256) = | 61 mA > A.C. | ON |

Notice that after execution of Pulses 7 and 8 it is determined that the activation current must lie between 59 and 61 mA, so that the only possible conclusion can be that air is present at the probe. After pulse 8 the cycle would be repeated in the same order so long as the probe is immersed in air.

Now consider that the probe suddenly becomes immersed in the hydrocarbon so that the activation current has changed from 60 mA to 460 mA. The interpolation pulses would again begin at 300 mA and would proceed as follows:

| Cycle 2: Probe Immersed in Hydrocarbon (A.C. = 460 mA) | | |
|---|---|---|
| Calculation of Current | Current to LED | Detector Status |
| Pulse 1 = 0 + (600/2) = | 300 mA < A.C. | OFF |
| Pulse 2 = 300 − (600/4) = | 450 mA < A.C. | OFF |
| Pulse 3 = 450 − (600/8) = | 525 mA > A.C. | ON |
| Pulse 4 = 525 − (600/16) = | 487 mA > A.C. | ON |
| Pulse 5 = 487 + (600/32) = | 468 mA > A.C. | ON |
| Pulse 6 = 468 + (600/64) = | 458 mA < A.C. | OFF |
| Pulse 7 = 458 − (600/128) = | 462 mA > A.C. | ON |
| Pulse 8 = 462 + (600/256) = | 459 mA < A.C. | OFF |

Thus, from inspection of the above, after execution of Pulses 7 and 8, it is ascertained that the activation current is between 459 mA and 462 mA and application of the calibration data would identify the fluid as being the hydrocarbon.

It is important to note the difference in the number of pulses required to identify the hydrocarbon using the ramp mode and the interpolation. For a ramp between 0 to 600 mA at 5 mA increments from pulse-to-pulse, the ramp mode would require 92 pulses to reach 460 mA. The interpolation mode requires only 8 pulses, a difference of a factor of 11. The reduction in the requisite number of pulses not only permits rapid fluid identification, but also increases the operating lifetime of the LED by reducing the required frequency of pulses, and allows the LED to be operated at higher intensities without exceeding the recommended duty cycle of the LED which increases permissible overall operating lengths.

Operation

Figure 4:
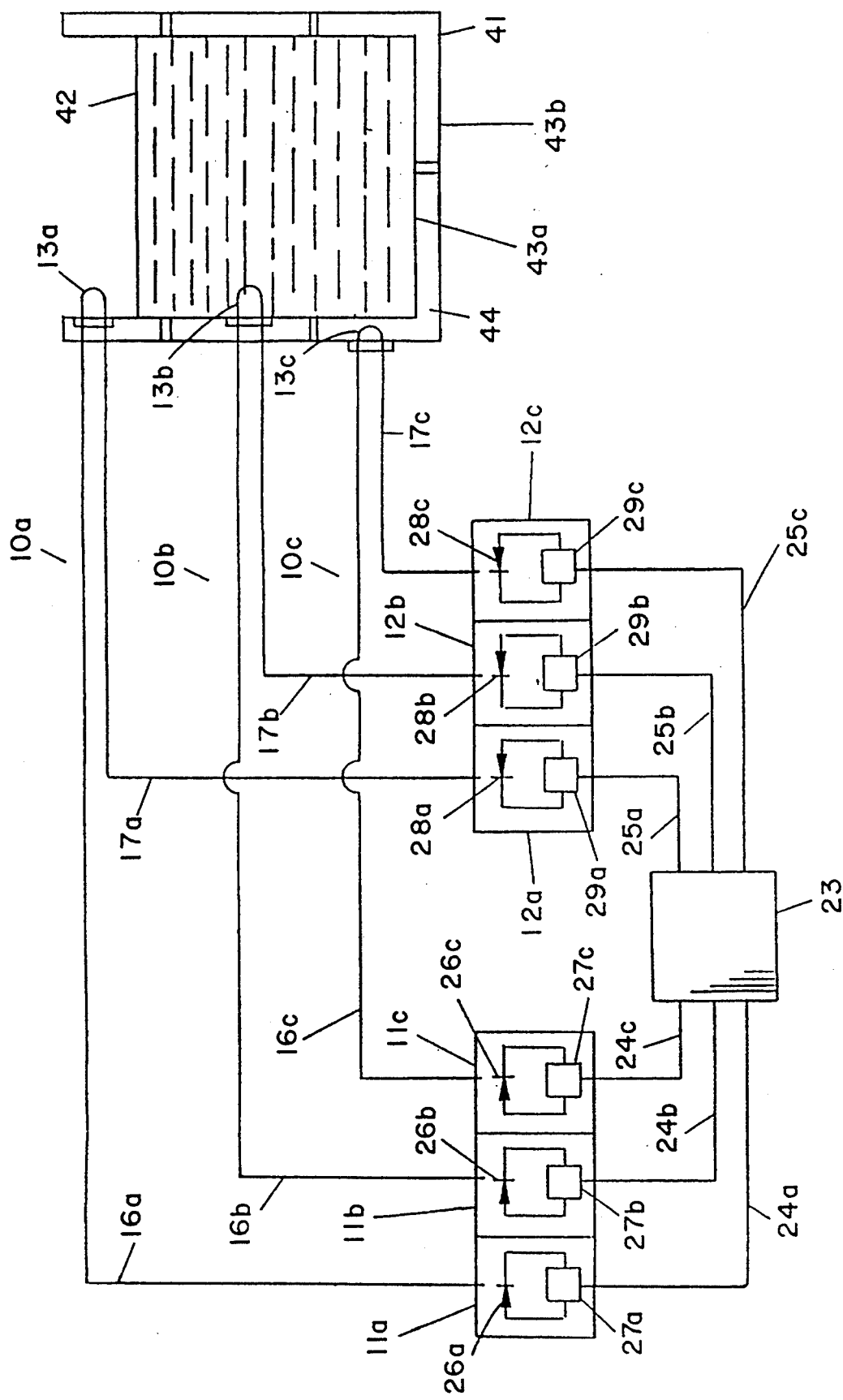
FIG. 4 is a schematic diagram illustrating the use of the present sensor system for liquid level measurement and interstitial leakage detection.

The sensor system of the present invention may be employed for liquid level detection, and interstitial leakage detection as illustrated in FIG. 4. Storage tank 41 is used to store hydrocarbon liquid 42, and has inner wall 43a and outer wall 43b defining interstitial space 44. The space above the liquid is occupied by air. Sensors 10a and 10b are deployed as liquid level sensors and probe 10c is used for interstitial leakage detection of hydrocarbon 42. Sensor 10a may be used to provide a high level indication and 10b a low level indication. Below, reference letters a, b, and c are used to designate components belonging to sensor 10a, 10b, or 10c, respectively. An important safety advantage of the present sensor is the optical principle of operation, particularly in the presence of a combustible hydrocarbon where the use of electronic sensors would require additional safeguard measures.

Probes 13a and 13b are mounted in inner wall 43a using a threaded sealing bushing 15 (not shown) as has been described in relation to FIG. 1. Probe 13c is similarly mounted in outer wall 43b with the probe tip in interstitial space 44. Probes 13a, 13b, and 13c are connected via inlet fiber optics 16a, 16b, and 16c, respectively, to light sources 11a, 11b, and 11c, each source comprising, respectively, current supply 27a, 27b, and 27c, and LED 26a, 26b, and 26c. Probes 13a, 13b, and 13c are connected to detectors 12a, 12b, and 12c, respectively, by fiber optics 17a, 17b, and 17c. Detectors 12a, 12b, and 12c comprise, respectively, photodiodes 28a, 28b, and 28c, and threshold circuitry 29a, 29b, and 29c. Microprocessor 23 is connected to light sources 11a, 11b, and 11c by cables 24a, 24b, and 24c, respectively, and to detectors 13a, 13b, and 13c by cables 25a, 25b, and 25c, respectively, Microprocessor 23 controls sensors 10a, 10b, and 10c, sequentially according to the methods described above in relation to a single sensor. The microprocessor and sensors can be operated in either the Ramp, Reverse Ramp, or the Interpolation Mode for identification of the fluid. Prior to installation, each sensor will have been independently calibrated for air, water, and hydrocarbon 42 and these calibration activation current data will be stored in the microprocessor memory for fluid identification as has been described. It is important for sensor 10c to be calibrated for water since it is common for water to accumulate intermittently in interstitial spaces due to condensation or invasion of rain or groundwater. Thus a sensor capable of only differentiating a vapor from a liquid, and nothing more, may give false indications of leakage of hydrocarbon 42.

Sensors 10a and 10b provide means for remotely controlling the level of liquid 42 in tank 41. Microprocessor 23 can be interfaced to peripheral hardware such as electronic valve actuators and pumps for controlling addition or drainage of liquid 42 from the tank as needed in response to the level indications from sensors 10a and 10b. Sensors 10a and 10b may also serve to signal the presence of water in the tank which may occur due to tank deterioration and leakage of water into the tank.

While three sensor systems are illustrated in FIG. 4, in practice additional probes may be employed and simultaneously controlled by microprocessor 23. Additional probes may be mounted at various elevations to give better resolution of liquid level, as well as sensors distributed within interstitial space 44.

Figure 5:
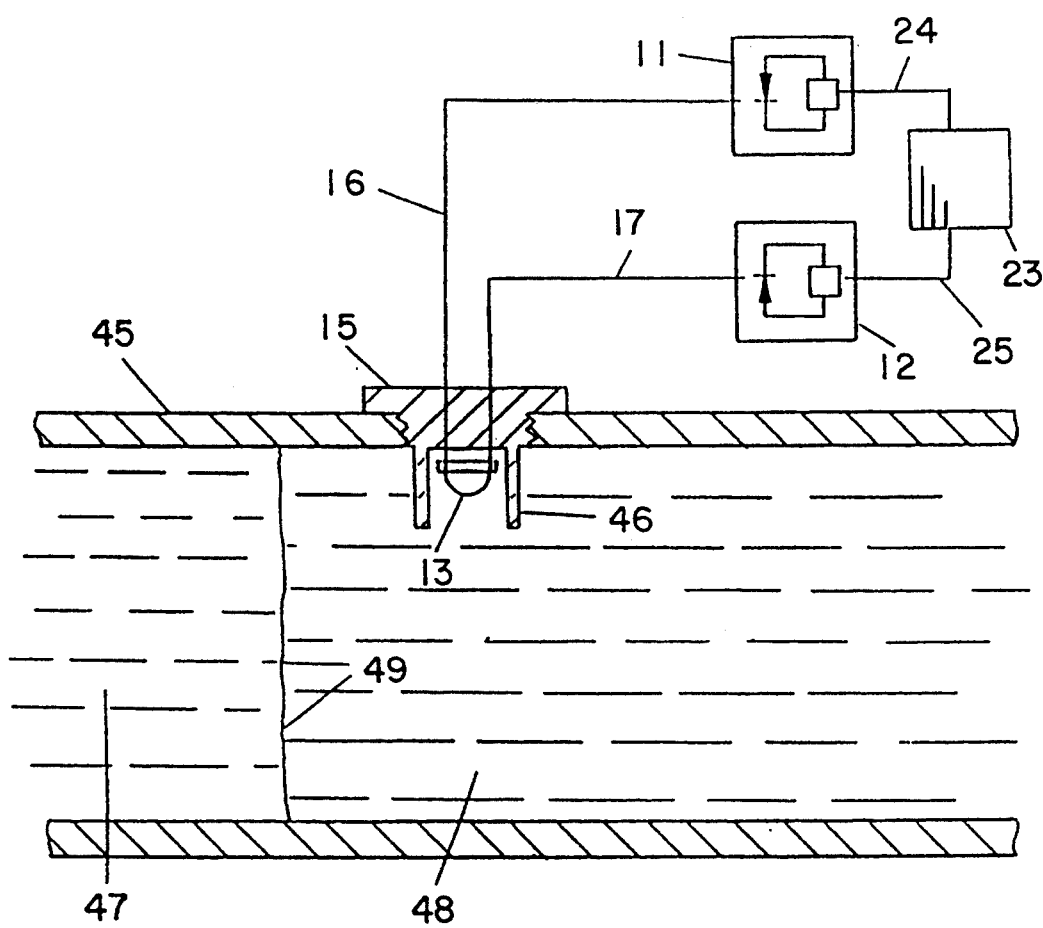
FIG. 5 is a schematic diagram illustrating the use of the present sensor system for pipeflow applications.

FIG. 5 illustrates the present sensor system for use in fluid identification in pipeflow applications.

Sensor 10 comprises probe 13 mounted in the wall of pipe 45 using threaded sealing bushing 15. In this application, bushing 15 may be provided with shroud 46 which provides protection of probe 13 from the flow environment. Alternatively, probe 13 may be mounted in a tee section spliced into the pipe. Probe 13 is connected to light source 11 and detector 12 by fiber optics 16 and 17 as has been described. Prior to installation probe 13 has been calibrated for each fluid to be monitored in pipe 45 and these data stored in the memory of microprocessor 23. Microprocessor 23 and sensor 10 are operated preferably in the Interpolation Mode for rapid fluid identification.

Regardless of the particular application, all of the sensor systems operate generally the same. A probe is initially in contact with a homogenous fluid having a uniform index of refraction. The light source is activated to produce a series of variable intensity light pulses of magnitudes between prescribed minimum and maximum limits. The sequence, of course, will depend on the mode employed (i.e. Ramping, Reverse Ramping, or Interpolation). The sequence of light pulses are transmitted from the source to the probe where they are attenuated. Inasmuch as the degree of attenuation of each pulse is approximately constant, the detector receives from the probe a corresponding sequence of attenuated light pulses which differ in intensity. The on/off or threshold intensity of the detector is set to have a value intermediate to the minimum and maximum intensities of the sequence of light pulses arriving from the probe, so that at a particular point in the sequence the detector will switch from off to on. The particular pulse in the sequence which activates the detector will correspond to a unique value of the input electrical current to the light source which produced the pulse, which has been referred to as the activation current. Because the amount of attenuation at the probe is proportional to the index of refraction of the fluid surrounding the probe, the activation current to the light source will be different for fluids having different refractive indices. For example, because a liquid generally has a higher index of refraction than a vapor, a liquid will attenuate more light than a vapor and thus will require a higher activation current to activate the detector. By comparing the identified activation level of the light detector with a calibrated scale, the fluid in contact with the probe can be determined.

What is claimed is:

1. A fluid sensor system for identifying fluids having different refractive indices, comprising:
   (a) a light source for producing light pulses;
   (b) a light detector having a predetermined threshold intensity, the detector further having an indication of whether a detected light pulse has an intensity below or above the threshold intensity;
   (c) a light transmitting probe for transmitting light pulses from the source to the detector, the probe having a first end in optical communication with the source to receive light pulses therefrom, an intermediate region in contact with a fluid to be identified, and a second end in optical communication with the detector to transmit light pulses thereto, the intermediate region having a property responsive to the index of refraction of the contacting fluid so that light pulses transmitted through the intermediate region are attenuated in proportion to the index of refraction of the fluid;
   (d) means for varying the intensity of light pulses produced by the light source to adjust the intensity of the emitted light pulses to an intensity level corresponding to the detector threshold intensity.

2. The apparatus of claim 1 wherein the detector comprises a photodiode.

3. The apparatus of claim 1 wherein the probe is a fiber optic having a core and a cladding, and the intermediate region comprises a region wherein the core is in contact with the fluid to be identified.

4. The apparatus of claim 1 further comprising means for comparing the adjusted intensity level of the emitted light pulses to a standard thereby identifying the fluid in contact with the probe.

5. The apparatus of claim 1 wherein the light source comprises a light emitting diode having a light intensity output proportional to an electrical input signal.

6. The apparatus of claim 5 wherein the input signal is electrical current and means for controlling the light source comprises a variable current pulse source.

7. The apparatus of claim 6 wherein the current pulse source produces pulses varying functionally as selected from the group consisting of (a) a ramp, (b) a reverse ramp, or (c) an interpolation.

8. A method of identifying a fluid selected from at least two different fluids in a container or pipe, which comprises:
   (a) positioning a refractometer probe in the container or pipe in contact with the fluid;
   (b) transmitting a series of light pulses to the refractometer probe;
   (c) receiving light signals which pass through the probe with a light detector, said detector being activated at a predetermined threshold intensity;
   (d) varying the light intensity of the light pulses until the activation level of the light detector is determined, the activation level indicating the identity of the fluid in contact with the probe.

9. The method of claim 8 and further comprising comparing the activation level of the light detector with a calibrated scale.

10. The method of claim 8 wherein the probe is positioned in a tank and the fluids include a gas and a liquid.

11. The method of claim 8 wherein the probe is positioned in a pipeline and the fluids include two hydrocarbon liquids.

12. A method of distinguishing between two fluids in a container or pipe having a refractometer probe disposed therein and in communication with a light source for receiving light pulses therefrom and a light detector for transmitting light thereto, said method comprising
   (a) determining the light intensity transmitted from the light source through the probe and to the detector to reach a predetermined threshold intensity for the probe in contact with one of the two fluids and for the probe in contact with the other fluid;
   (b) thereafter determining which fluid is in contact with the probe by varying the intensity of light pulses through the probe until the predetermined threshold intensity is reached; and
   (c) comparing the level measured in step (b) with the levels determined in step (a) for each of the two fluids.

13. A method of detecting a change of fluid flowing in a pipe which comprises:
   (a) disposing a refractometer probe in the pipe in contact with the fluid;
   (b) passing light pulses of variable intensity through the probe;
   (c) receiving light pulses from the probe with a detector having a light activation level;
   (d) determining the light intensity of light pulses transmitted to the probe to achieve a predetermined threshold intensity of light pulses received by the detector to activate the detector; and
   (e) repeating steps (c) and (d), a change in the level of light pulse transmitted to the probe to activate the detector indicating a change of fluid in contact with the probe.

14. A method of identifying fluids which comprises:
   (a) positioning a refractometer probe in a vessel or pipeline;
   (b) connecting the probe in series with
      (i) a light source for transmitting a series of light pulses to the probe, and
      (ii) a light detector for receiving light pulses from the probe and being activated at a predetermined light intensity level;
   (c) contacting the probe in the vessel or pipeline with a fluid selected from fluids having different refractive indices;
   (d) varying the light intensity pulses transmitted to the probe and the light detector until the light intensity for activating the light detector is determined; and
   (e) comparing the activation light intensity of the light transmitted from the light source as determined in step (d) with a calibrated scale of activation light intensity for the selected fluids to match the activation light intensity determined in step (d) with an activation light intensity on the calibrated scale thereby identifying the fluid in contact with the probe.

15. The method of claim 14 wherein the light source is an LED having an output proportional to input current.

* * * * *